United States Patent
Guimaraes et al.

(12) 
(10) Patent No.: US 6,425,905 B1
(45) Date of Patent: Jul. 30, 2002

(54) METHOD AND APPARATUS FOR FACILITATING REMOVAL OF A CORNEAL GRAFT

(75) Inventors: Ricardo Guimaraes, Belo Horizonte (BR); Rod Ross; Gregg Hughes, both of Mission Viejo, CA (US)

(73) Assignee: Med-Logics, Inc., Laguna Niguel, CA (US)

( * ) Notice: Subject to any disclaimer, the term of this patent is extended or adjusted under 35 U.S.C. 154(b) by 0 days.

(21) Appl. No.: 09/726,959

(22) Filed: Nov. 29, 2000

(51) Int. Cl.⁷ .................................................. A61F 9/007
(52) U.S. Cl. ........................................................ 606/166
(58) Field of Search ................................. 606/166, 107

(56) References Cited

U.S. PATENT DOCUMENTS

| | | |
|---|---|---|
| 1,841,968 A | 1/1932 | Lowry |
| 1,847,658 A | 3/1932 | Lasker |
| 2,070,281 A | 2/1937 | Leggiadro |
| 2,480,737 A | 8/1949 | Jayle |
| RE23,496 E | 5/1952 | Seeler |
| 2,708,437 A | 5/1955 | Hutchins |
| 2,824,455 A | 2/1958 | Ristow et al. |
| 3,033,196 A | 5/1962 | Hay |
| 3,252,623 A | 5/1966 | Corbin et al. |
| 3,266,494 A | 8/1966 | Brownrigg et al. |
| 3,308,828 A | 3/1967 | Pippin |
| 3,399,677 A | 9/1968 | Gould et al. |
| 3,511,162 A | 5/1970 | Truhan |

(List continued on next page.)

FOREIGN PATENT DOCUMENTS

| | | |
|---|---|---|
| DE | 25 47 185 | 4/1977 |
| EP | 1033 120 A2 | 9/2000 |
| FR | 2 549 727 | 7/1963 |

OTHER PUBLICATIONS

Steinway Instrument Company Inc., The Steinway/Barraquer in–Situ Microkeratome Set.

Brochure, Site TXR Systems, Site Mycrosurgical Systems, Inc., Horsham, Pennsyvania.

Marshall M. Parks, "Intracapsular Aspiration" article, pp. 59–74.

Van Oldenborgh, "Correction of late operative complications by means of a suction cutter", Opthal. Soc. U.K. (1980), 100, 219, pp. 219–221.

Helfgott, M.D. "A System for Variable Aspiration of Material Dissected from the Posterior Chamber", Ophthalmic Surgery, vol. 15, Jun. 1984, pp. 529–350.

Coopervision Brochure on Cavitron/Kelman Model 6500 E.I.S. and Model 7500 6 pages.

Surgical Design Brochure on "The Ocusystem", 1 page.

Coopervision Brochure on "Cavitorn/Kelman Phaco–Emulsifier Aspirator Model 8001", 2 pages.

(List continued on next page.)

*Primary Examiner*—Kennedy Schaetzle
(74) *Attorney, Agent, or Firm*—Irell & Manella, LLP

(57) ABSTRACT

The invention relates to an artificial chamber that can support and pressurize a donor cornea to extract a corneal graft. The artificial chamber has a stationary stem that is adapted to support a cornea. The stem has an inner channel that allows air to pressurize the cornea. The artificial chamber has an outer cap that can be moved in a downward direction to secure the cornea. The cap has an opening that exposes a portion of the cornea to allow for the extraction of a corneal graft. The outer cap is attached to an outer sleeve that is moved by rotation of a cam. The chamber includes a spring that exerts a clamping force onto the cornea. The clamping force can be adjusted by rotating an adjustment wheel. The adjustable spring force allows an operator to set a desired clamping force that is then repeated for each grafting procedure.

14 Claims, 1 Drawing Sheet

U.S. PATENT DOCUMENTS

| | | |
|---|---|---|
| 3,561,429 A | 2/1971 | Jewett |
| 3,583,403 A | 6/1971 | Pohl |
| 3,589,363 A | 6/1971 | Banko |
| 3,624,821 A | 11/1971 | Henderson |
| 3,693,613 A | 9/1972 | Kelman |
| 3,723,030 A | 3/1973 | Gelfand |
| 3,752,161 A | 8/1973 | Bent |
| 3,763,862 A | 10/1973 | Spieth |
| 3,812,855 A | 5/1974 | Banko |
| 3,815,604 A | 6/1974 | O'Malley et al. |
| 3,841,799 A | 10/1974 | Spinosa et al. |
| 3,842,839 A | 10/1974 | Malis et al. |
| 3,882,872 A | 5/1975 | Douvas et al. |
| 3,884,238 A | 5/1975 | O'Malley et al. |
| 3,899,829 A | 8/1975 | Storm et al. |
| 3,903,881 A | 9/1975 | Weigl |
| 3,913,584 A | 10/1975 | Walchle et al. |
| 3,920,014 A | 11/1975 | Banko |
| 3,930,505 A | 1/1976 | Wallach |
| 3,977,425 A | 8/1976 | Hayashida |
| 3,982,539 A | 9/1976 | Muriot |
| 3,983,474 A | 9/1976 | Kuipers |
| 3,986,512 A | 10/1976 | Walliser |
| 4,004,590 A | 1/1977 | Muriot |
| 4,011,869 A | 3/1977 | Seiler, Jr. |
| 4,034,712 A | 7/1977 | Duncan |
| 4,043,342 A | 8/1977 | Morrison, Jr. |
| 4,108,182 A | 8/1978 | Hartman et al. |
| 4,135,515 A | 1/1979 | Muriot |
| 4,137,920 A | 2/1979 | Bonnet |
| 4,168,707 A | 9/1979 | Douvas et al. |
| 4,173,980 A | 11/1979 | Curtin |
| 4,178,707 A | 12/1979 | Littlefield |
| 4,204,328 A | 5/1980 | Kutner |
| 4,205,682 A | 6/1980 | Crock et al. |
| 4,210,146 A | 7/1980 | Banko |
| 4,217,993 A | 8/1980 | Jess et al. |
| 4,223,676 A | 9/1980 | Wuchinich et al. |
| 4,245,815 A | 1/1981 | Willis |
| 4,246,902 A | 1/1981 | Martinez |
| 4,274,411 A | 6/1981 | Dotson, Jr. |
| 4,301,802 A | 11/1981 | Poler |
| 4,304,262 A | 12/1981 | Icking |
| 4,308,385 A | 12/1981 | Goorden |
| 4,308,835 A | 1/1982 | Abbey |
| 4,314,560 A | 2/1982 | Helfgott et al. |
| 4,319,899 A | 3/1982 | Marsh |
| 4,320,761 A | 3/1982 | Haddad |
| 4,344,784 A | 8/1982 | Deckas et al. |
| 4,354,838 A | 10/1982 | Hoyer et al. |
| 4,395,258 A | 7/1983 | Wang et al. |
| 4,396,386 A | 8/1983 | Kurtz et al. |
| 4,427,427 A | 1/1984 | DeVecchi |
| 4,428,748 A | 1/1984 | Peyman et al. |
| 4,429,696 A | 2/1984 | Hanna |
| 4,445,517 A | 5/1984 | Feild |
| 4,474,411 A | 10/1984 | Peters et al. |
| 4,475,904 A | 10/1984 | Wang |
| 4,476,862 A | 10/1984 | Pao |
| 4,479,717 A | 10/1984 | Cornillault |
| 4,481,948 A | 11/1984 | Sole |
| 4,493,695 A | 1/1985 | Cook |
| 4,493,698 A | 1/1985 | Wang et al. |
| 4,522,371 A | 6/1985 | Fox et al. |
| 4,523,911 A | 6/1985 | Braetsch et al. |
| 4,524,948 A | 6/1985 | Hall |
| 4,530,357 A | 7/1985 | Pawloski et al. |
| 4,531,934 A | 7/1985 | Kossovsky et al. |
| 4,540,406 A | 9/1985 | Miles |
| 4,555,645 A | 11/1985 | Atkinson |
| 4,560,395 A | 12/1985 | Davis |
| 4,589,414 A | 5/1986 | Yoshida et al. |
| 4,598,729 A | 7/1986 | Naito et al. |
| 4,647,209 A | 3/1987 | Neukomm et al. |
| 4,660,566 A | 4/1987 | Swinger et al. |
| 4,660,970 A | 4/1987 | Ferrano |
| 4,662,370 A | 5/1987 | Hoffmann et al. |
| 4,665,914 A | 5/1987 | Tanne |
| 4,674,499 A | 6/1987 | Pao |
| 4,674,503 A | 6/1987 | Peyman et al. |
| 4,678,459 A | 7/1987 | Onik et al. |
| 4,688,570 A | 8/1987 | Kramer et al. |
| 4,690,099 A | 9/1987 | Gregan et al. |
| 4,701,049 A | 10/1987 | Beckmann et al. |
| 4,705,395 A | 11/1987 | Hageniers |
| 4,706,687 A | 11/1987 | Rogers |
| 4,723,545 A | 2/1988 | Nixon et al. |
| 4,743,770 A | 5/1988 | Lee |
| 4,757,814 A | 7/1988 | Wang et al. |
| 4,767,403 A | 8/1988 | Hodge |
| 4,768,506 A | 9/1988 | Parker et al. |
| 4,770,654 A | 9/1988 | Rogers et al. |
| 4,782,239 A | 11/1988 | Hirose et al. |
| 4,782,849 A | 11/1988 | Hodge |
| 4,791,934 A | 12/1988 | Brunnett |
| 4,805,615 A | 2/1989 | Carol |
| 4,805,616 A | 2/1989 | Pao |
| 4,807,623 A | 2/1989 | Lieberman |
| 4,819,635 A | 4/1989 | Shapiro |
| 4,825,091 A | 4/1989 | Breyer et al. |
| 4,828,306 A | 5/1989 | Blatt |
| 4,830,047 A | 5/1989 | Hodge |
| 4,837,857 A | 6/1989 | Scheller et al. |
| 4,838,281 A | 6/1989 | Rogers et al. |
| 4,840,175 A | 6/1989 | Peyman |
| 4,865,033 A * | 9/1989 | Krumeich et al. ........... 606/166 |
| 4,884,570 A * | 12/1989 | Krumeich et al. ........... 606/166 |
| 4,886,085 A | 12/1989 | Miller |
| 4,903,695 A | 2/1990 | Warner et al. |
| 4,909,815 A | 3/1990 | Meyer |
| RE33,250 E | 7/1990 | Cook |
| 4,943,289 A | 7/1990 | Goode et al. |
| 4,965,417 A | 10/1990 | Massie |
| 4,988,347 A | 1/1991 | Goode et al. |
| 4,997,437 A | 3/1991 | Grieshaber |
| 5,011,482 A | 4/1991 | Goode et al. |
| 5,013,310 A | 5/1991 | Goode et al. |
| 5,019,076 A | 5/1991 | Yamanashi et al. |
| 5,059,204 A | 10/1991 | Lawson et al. |
| 5,083,558 A | 1/1992 | Thomas et al. |
| 5,092,874 A * | 3/1992 | Rogers ...................... 606/166 |
| 5,106,364 A | 4/1992 | Hayafuji et al. |
| 5,133,713 A | 7/1992 | Huang et al. |
| 5,133,726 A | 7/1992 | Ruiz et al. |
| 5,176,628 A | 1/1993 | Charles et al. |
| 5,201,749 A | 4/1993 | Sachse et al. |
| 5,207,683 A | 5/1993 | Goode et al. |
| 5,215,104 A | 6/1993 | Steinert |
| 5,217,459 A | 6/1993 | Kamerling |
| 5,226,910 A | 7/1993 | Kajiyama et al. |
| 5,242,404 A | 9/1993 | Conley et al. |
| 5,271,379 A | 12/1993 | Phan et al. |
| 5,273,406 A | 12/1993 | Feygin |
| 5,273,524 A | 12/1993 | Fox et al. |
| 5,285,795 A | 2/1994 | Ryan et al. |
| 5,322,505 A | 6/1994 | Krause et al. |
| 5,330,470 A | 7/1994 | Hagen |
| 5,354,268 A | 10/1994 | Peterson et al. |
| 5,364,395 A | 11/1994 | West, Jr. |
| 5,374,188 A | 12/1994 | Frank et al. |
| 5,380,280 A | 1/1995 | Peterson |

| | | |
|---|---|---|
| 5,383,454 A | 1/1995 | Bucholz |
| 5,395,368 A | 3/1995 | Ellman et al. |
| 5,403,276 A | 4/1995 | Schechter et al. |
| 5,403,311 A | 4/1995 | Abele et al. |
| 5,437,678 A | 8/1995 | Sorensen |
| 5,465,633 A | 11/1995 | Bernloehr |
| 5,474,532 A | 12/1995 | Steppe |
| 5,476,448 A | 12/1995 | Urich |
| 5,476,473 A | 12/1995 | Heckele |
| 5,496,339 A | 3/1996 | Koepnick |
| 5,507,751 A | 4/1996 | Goode et al. |
| 5,520,684 A | 5/1996 | Imran |
| 5,527,332 A | 6/1996 | Clement |
| 5,527,356 A | 6/1996 | Peyman et al. |
| 5,531,744 A | 7/1996 | Nardella et al. |
| 5,556,397 A | 9/1996 | Long et al. |
| 5,566,681 A | 10/1996 | Manwaring et al. |
| RE35,421 E | 1/1997 | Ruiz et al. |
| D377,524 S | 1/1997 | Lipp |
| 5,611,799 A | 3/1997 | Smith |
| 5,624,394 A | 4/1997 | Barnitz et al. |
| 5,643,304 A | 7/1997 | Schechter et al. |
| 5,693,013 A | 12/1997 | Geuder |
| 5,700,240 A | 12/1997 | Barwick, Jr. et al. |
| 5,704,927 A | 1/1998 | Gillette et al. |
| 5,738,677 A | 4/1998 | Colvard et al. |
| 5,779,723 A | 7/1998 | Schwind |
| 5,782,849 A | 7/1998 | Miller |
| 5,787,760 A | 8/1998 | Thorlakson |
| 5,795,328 A | 8/1998 | Barnitz et al. |
| 5,810,857 A | 9/1998 | Mackool |
| 5,814,010 A | 9/1998 | Ziegler |
| 5,817,075 A | 10/1998 | Giungo |
| 5,868,728 A | 2/1999 | Giungo et al. |
| 5,916,330 A | 6/1999 | Jacobson |
| 5,941,250 A | 8/1999 | Aramant et al. |
| 5,944,731 A | 8/1999 | Hanna |
| 5,957,921 A | 9/1999 | Mirhashemi et al. |
| 5,989,272 A | 11/1999 | Barron et al. |
| 6,013,049 A | 1/2000 | Rockley et al. |
| 6,019,754 A | 2/2000 | Kawesch |
| 6,045,563 A | 4/2000 | Duprat |
| 6,051,009 A | 4/2000 | Hellenkamp et al. |
| 6,059,805 A | 5/2000 | Sugimura et al. |
| 6,083,236 A | 7/2000 | Feingold |
| 6,086,544 A | 7/2000 | Hibner et al. |
| 6,132,446 A * | 10/2000 | Hellenkamp et al. ....... 606/166 |
| 6,165,189 A | 12/2000 | Ziemer |

OTHER PUBLICATIONS

Coopervision Brochure on Cavitron/Kelman Phaco–Emulsifier Aspirator Model 9001, 6 pages.

Greishaber of Switzerland Brochure on "MPC, The Membrane Peeler Cutter", 5 pages.

Micro–Vit Vitrectomy System Product Brochure and Instruction Manual.

Storz Irrigation Aspiration System Product Brochure and Instruction Manual.

United Surgical Corporation Brochure on "Phacotron Plus", one page.

Surgical Design Company Brochure on Keates Ultrasonic I/E Mini Probe by A. Banko, 2 pages.

Surgical Design Corporation Brochure on U.S., Phaco System, 1 page.

Coopervision Brochure on System VI, 1 page.

Murayama et al. "A Portable Air Driving Unit for Blood Pumps", Japanese Journal of Artificial Organs, vol. 14, No. 3, pp. 1206–1209 (English Translation).

Scuderi, et al., French article entitled "La Chirurgie de la Cartaracte Congenitale", pp. 174–185. (English translation).

Hayashi et al., Japanese Experience with Ventricular Assist Devices IBEE Engineering in Medicine and Biology Magazine Mar. 1986, pp. 30–36.

Grieshaber and Co. of Switzerland, "Sutherland Rotatable Intraocular Microscissors", 2 pages.

JCERS and Tissue Removal Systems, Diskecter™ System, Rapid Tissue Removal System advertisement.

Charles and Wang, "A Linear Suction Control for the Vitreous Cutter (Ocutome)", Arch. Ophthalmol. vol. 99, Sep. 1981, p. 1631.

Crosby, "On Control of Artificial Hearts", pp. 89–114.

Mrava, Cardiac Engineering, vol. 3, pp. 31–68.

* cited by examiner

METHOD AND APPARATUS FOR FACILITATING REMOVAL OF A CORNEAL GRAFT

BACKGROUND OF THE INVENTION

1. Field of the Invention

The present invention relates to an artificial chamber that is used to support and pressurize a donor cornea to facilitate the removal of a corneal graft.

2. Background Information

There have been developed various techniques to correct the vision of a patient. For example, there is a medical procedure that varies the curvature of a cornea using a laser. This technique is commonly referred to as Las in situ Keratomileusis (LASIK).

A LASIK procedure is performed by initially cutting a flap in the cornea to expose the stroma layer of the eye. A laser beam is then directed onto the stroma to ablate corneal tissue. After ablation the flap is placed back onto the stroma. The result is a variation in the refractive characteristics of the eye.

The flap may become severed from the cornea either during or after the procedure. This may require obtaining another flap from a donor eye that must then be attached to the patient's cornea. To create a replicant corneal flap the donor corneal must be pressurized to create the proper radius of curvature. Therefore, to create a flap the donor cornea must not only be secured but also pressurized.

U.S. Pat. No. 6,045,563 issued to Duprat and assigned to Moria SA ("Moria"), discloses an artificial chamber that can be used to support and pressurize a cornea to extract a corneal graft. The Moria chamber includes a clamping cap that can be removed from a chamber stand to expose an internal stem. The donor cornea can be placed onto a pedestal portion of the internal stem. The clamping cap is then reattached to the stand.

An operator rotates a thumb wheel that moves the stem in an upward direction until the cornea engages the bottom surface of the clamping cap. The cornea is pressurized with air that flows through a center channel of the stem. A portion of the pressurized donor cornea extends through an opening in the clamping cap. A keratome can be attached to the cap and actuated to slice a graft from the cornea.

The Moria artificial chamber requires the operator to rotate the wheel until the cornea is secured to the clamping cap. This manual actuation may result in a deficient, or an excessive, clamping force on the cornea. It is desirable to have a clamping force that is the same for each procedure. The Moria patent discloses a second pneumatically actuated embodiment that would provide a repeatable clamping force, but the pressure required to move the stem may be less, or more, than the desired clamping force exerted onto the cornea. It would be desirable to provide an artificial chamber that can provide a repeatable desired clamping force on a cornea during a grafting procedure.

BRIEF SUMMARY OF THE INVENTION

One embodiment of the present invention is an artificial chamber that can be used to support and pressurize a cornea to extract a corneal graft. The artificial chamber may include a stem that is attached to a stand. The stem is adapted to support and pressurize a cornea. The chamber may further have an outer sleeve and a cap that can move relative to the stem. The sleeve and cap can be moved by an actuator to secure the cornea.

DETAILED DESCRIPTION OF THE PREFERRED EMBODIMENT

In general the present invention provides an artificial chamber that can support and pressurize a donor cornea to extract a corneal graft. The artificial chamber has a stationary stem that is adapted to support a cornea. The stem has an inner channel that allows air to pressurize the cornea. The artificial chamber has an outer cap that can be moved in a downward direction to secure the cornea. The cap has an opening that exposes a portion of the cornea to allow for the extraction of a corneal graft. The outer cap is attached to an outer sleeve that is moved by rotation of a cam. The chamber includes a spring that exerts a clamping force onto the cornea. The clamping force can be adjusted by rotating an adjustment wheel. The adjustable spring force allows an operator to set a desired clamping force that is then repeated for each grafting procedure.

Figure 1:
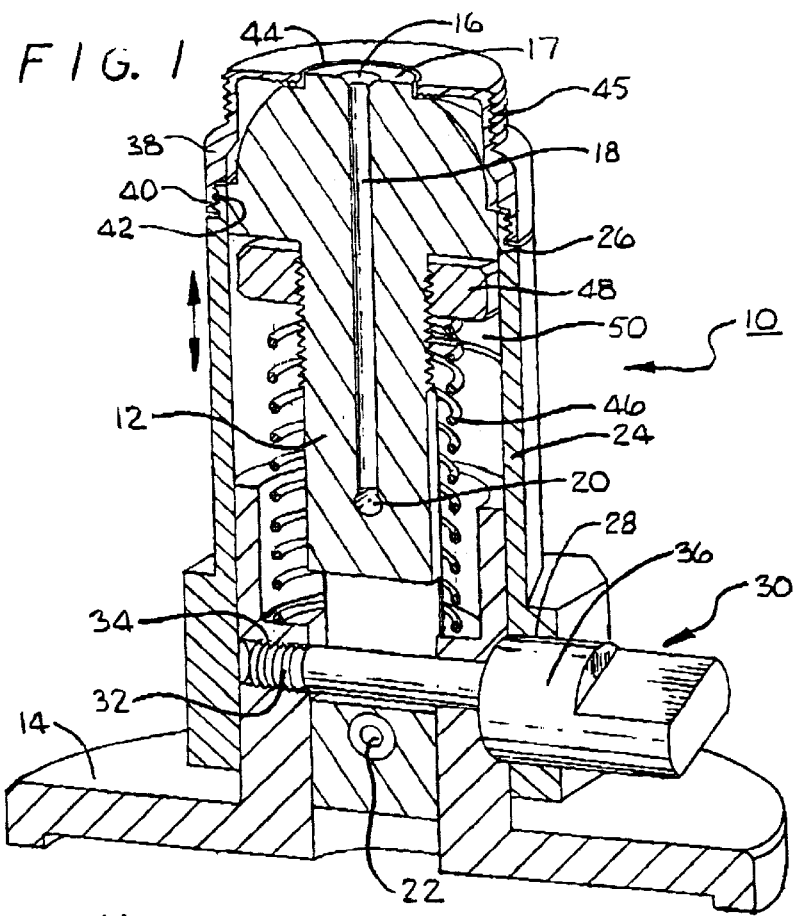
FIG. 1 is a cross-sectional view of an embodiment of an artificial chamber of the present invention.

Referring to the drawings more particularly by reference numbers, FIG. 1 shows an embodiment of an artificial chamber 10 of the present invention. The artificial chamber 10 may include a stem 12 that is coupled to a stand 14. The stem 12 is coupled in a manner to allow movement relative to the stand 14. The stem 12 may have a countersunk opening 16 in a pedestal portion 17. The countersink 16 and pedestal portion 17 are configured to support a cornea (not shown). The opening 16 may be in fluid communication with a center fluid channel 18. The fluid channel 18 may be in fluid communication with inlet/outlet ports 20 and 22. The inlet/outlet ports 20 and 22 are typically coupled to a source of pressurized air through a control valve (not shown). By way of example, the source of pressurized air may be an air line in a commercial building structure.

The artificial chamber 10 may further have an outer sleeve 24 that can move relative to the stem 12. The stem 12 may have an outer upper bearing surface 26 to insure translational movement of the outer sleeve 24. The outer sleeve 24 may include a slot 28 that receives an actuator 30. The actuator 30 may include a threaded stem portion 32 that screws into a corresponding threaded aperture 34 of the stand 14. The actuator 30 may also have a cam portion 36 that is off-center from the stem portion 32 so that rotation of the cam 36 moves the outer sleeve 24 in an up and down direction as indicated by the arrows.

An outer cap 38 is attached to the outer sleeve 24. The cap 38 may have internal threads 40 that screw onto corresponding external threads 42 of the outer sleeve 24. The cap 38 is adapted to engage and secure a donor cornea that is placed onto the pedestal portion 17 of the stem 12. The cap 38 further has an opening 44 that allows a portion of the donor cornea to be exposed so that a graft can be extracted from the cornea. The cap 38 may have an external thread 45 that allows a keratome to be attached to the chamber 10 and actuated to create the corneal graft.

The chamber 10 may further have a spring 46 that exerts a spring force onto stem 12. The spring force can be adjusted by rotating an adjustment wheel 48 that can vary the compression length of the spring 46. The adjustment wheel 48 can be accessed through an opening 50 in the outer sleeve 24. Rotating the wheel 48 varies the clamping force exerted by the cap 38 onto the cornea. The spring 46 and wheel 48 provide a mechanism to repeatedly provide a desired clamping force onto the cornea that is neither inadequate nor excessive.

Figure 2:
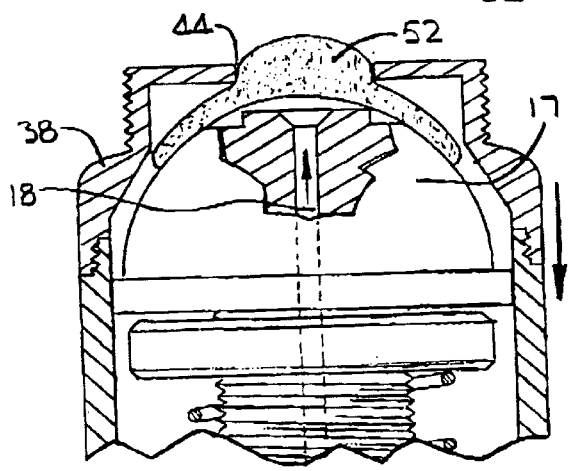
FIG. 2 is a cross-sectional view similar to FIG. 1 showing a cornea secured by the chamber.

In operation, the cap 38 is removed from the outer sleeve 24 and a cornea 52 is placed onto the pedestal portion 17 of the stem 12. The cap 38 is then reattached to the outer sleeve 24. As shown in FIG. 2, the actuator 30 is rotated to move the cap 38 down into the cornea 52. Air is then introduced to the inner channel 18 to pressurize the cornea 52. A portion of the cornea 52 will extend through the cap opening 44. An external device such as a keratome (not shown) can be attached to the cap 38 and actuated to extract a graft from the cornea 52. Once the graft is removed, the cornea 52 can be depressurized. The actuator 30 can then be rotated to move the cap 38 away from the donor cornea 52, wherein the cap 38 can be detached from the outer sleeve 24 and the cornea 52 removed from the stem 12 to complete the procedure.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An artificial chamber that can support a cornea to create a corneal graft, comprising:
   a stand;
   a stem attached to said stand, said stem having a pedestal portion adapted to support the cornea and an air channel that can be in fluid communication with the cornea;
   an outer sleeve;
   a cap attached to said outer sleeve; and,
   an actuator that can create relative movement between said outer sleeve and said cap, and said stem.

2. The artificial chamber of claim 1, further comprising a spring that exerts a biasing force on said stem.

3. The artificial chamber of claim 2, further comprising an adjustment wheel that is coupled to said spring.

4. The artificial chamber of claim 1, wherein said actuator includes a cam.

5. The artificial chamber of claim 1, wherein said cap has an opening.

6. The artificial chamber of claim 3, wherein said outer sleeve has an opening that provides access to said adjustment wheel.

7. An artificial chamber that can support a cornea to create a corneal graft, comprising:
   a stand;
   a stem attached to said stand, said stem having a pedestal portion adapted to support the cornea and an air channel that can be in fluid communication with the cornea;
   an outer sleeve that can move relative to said stem;
   a cap attached to said outer sleeve, said cap having an opening that can expose a portion of the cornea;
   a spring that exerts a biasing force on said stem; and,
   a cam that can be rotated to move said cap into the cornea.

8. The artificial chamber of claim 7, further comprising an adjustment wheel that is coupled to said spring.

9. The artificial chamber of claim 8, wherein said outer sleeve has an opening that provides access to said adjustment wheel.

10. A method for removing a corneal graft from a cornea, comprising:
    placing the cornea on a stem;
    actuating an actuator to move an outer sleeve and a cap relative to the stem until the cap engages and secures the cornea;
    pressurizing the cornea; and,
    removing a corneal graft from the cornea.

11. The method of claim 10, wherein the outer sleeve and the cap are moved by rotating a cam.

12. The method of claim 10, further comprising moving the cap away from the cornea and removing the cornea from the stem.

13. The method of claim 10, further comprising adjusting a spring force that is exerted by the stem onto the cornea.

14. The method of claim 13, wherein the spring force is adjusted by rotating an adjustment wheel.

* * * * *